(12) United States Patent
Altmann et al.

(10) Patent No.: US 9,308,041 B2
(45) Date of Patent: *Apr. 12, 2016

(54) LASSO CATHETER WITH ROTATING ULTRASOUND TRANSDUCER

(75) Inventors: Andres Claudio Altmann, Haifa (IL); Assaf Govari, Haifa (IL)

(73) Assignee: Biosense Webster (Israel) Ltd. (IL)

( * ) Notice: Subject to any disclaimer, the term of this patent is extended or adjusted under 35 U.S.C. 154(b) by 967 days.

This patent is subject to a terminal disclaimer.

(21) Appl. No.: 12/975,787

(22) Filed: Dec. 22, 2010

(65) Prior Publication Data

US 2012/0165667 A1 Jun. 28, 2012

(51) Int. Cl.

| | |
|---|---|
| A61B 18/14 | (2006.01) |
| A61B 8/08 | (2006.01) |
| A61B 8/12 | (2006.01) |
| A61B 8/00 | (2006.01) |
| A61B 5/042 | (2006.01) |
| A61B 5/06 | (2006.01) |
| A61B 18/00 | (2006.01) |
| A61B 19/00 | (2006.01) |
| A61M 25/01 | (2006.01) |

(52) U.S. Cl.
CPC ........... *A61B 18/1492* (2013.01); *A61B 5/0422* (2013.01); *A61B 5/061* (2013.01); *A61B 8/0883* (2013.01); *A61B 8/12* (2013.01); *A61B 8/445* (2013.01); *A61B 2018/00375* (2013.01); *A61B 2018/00577* (2013.01); *A61B 2018/00839* (2013.01); *A61B 2018/1435* (2013.01); *A61B 2018/1467* (2013.01); *A61B 2019/528* (2013.01); *A61B 2019/5251* (2013.01); *A61M 2025/0163* (2013.01)

(58) Field of Classification Search
CPC ................. A61B 18/1492; A61B 2018/00375; A61B 2018/00577; A61B 2018/00839; A61B 2018/1435; A61B 2018/1467; A61B 2018/5251; A61B 2019/528; A61B 5/0422; A61B 5/061; A61B 8/0883; A61B 8/12; A61B 8/445
USPC ................. 600/439, 459, 462, 466, 467, 471; 606/32, 38, 41; 604/22

See application file for complete search history.

(56) References Cited

U.S. PATENT DOCUMENTS

| | | |
|---|---|---|
| 5,076,278 A | 12/1991 | Vilkomerson et al. |
| 5,081,993 A | 1/1992 | Kitney et al. |

(Continued)

FOREIGN PATENT DOCUMENTS

| | | |
|---|---|---|
| JP | 2005-508695 A | 4/2005 |
| JP | 2005-137916 A | 6/2005 |

(Continued)

OTHER PUBLICATIONS

U.S. Appl. No. 12/649,417—pending.

(Continued)

*Primary Examiner* — Amanda Lauritzen Moher

(57) ABSTRACT

A medical device includes an insertion shaft, having a longitudinal axis and having a distal end adapted for insertion into a body of a patient. A resilient end section is fixed to the distal end of the insertion shaft and is formed so as to define an arc oriented obliquely relative to the axis and having a center of curvature on the axis. One or more electrodes are disposed along the end section. An ultrasound transducer is fixed to the distal end and is configured to image a vicinity of the arc using ultrasound waves.

15 Claims, 3 Drawing Sheets

(56) References Cited

U.S. PATENT DOCUMENTS

| | | | |
|---|---|---|---|
| 5,239,999 A * | 8/1993 | Imran | 600/374 |
| 6,064,902 A | 5/2000 | Haissaguerre et al. | |
| 6,669,693 B2 | 12/2003 | Friedman | |
| 6,802,840 B2 | 10/2004 | Chin et al. | |
| 6,973,339 B2 * | 12/2005 | Govari | 600/374 |
| 7,291,146 B2 | 11/2007 | Steinke et al. | |
| 7,477,763 B2 | 1/2009 | Willis et al. | |
| 8,357,152 B2 | 1/2013 | Govari et al. | |
| 8,475,450 B2 | 7/2013 | Govari et al. | |
| 8,608,735 B2 * | 12/2013 | Govari | A61B 18/1492 606/41 |
| 2003/0014037 A1 | 1/2003 | Thompson | |
| 2005/0033135 A1 * | 2/2005 | Govari | 600/374 |
| 2009/0024040 A1 * | 1/2009 | Cespedes | 600/467 |
| 2011/0190755 A1 * | 8/2011 | Mathur | A61B 18/1233 606/33 |
| 2013/0110104 A1 * | 5/2013 | Corvi | A61B 18/1492 606/41 |

FOREIGN PATENT DOCUMENTS

| | | |
|---|---|---|
| JP | 2005-529701 A | 10/2005 |
| JP | 2007-504910 A | 3/2007 |
| JP | 2010-131390 A | 6/2010 |
| WO | WO 96/05768 A1 | 2/1996 |
| WO | WO 2008/042423 A2 | 4/2008 |

OTHER PUBLICATIONS

AcuNav™ *Ideas Making a Difference, Intracardiac Echocardiography for Electrophysiology. Putting the Focus on Safety.* Biosense Webster, Inc. brochure 2006.

CartoSound™ *Ideas Making a Difference, The Future of Electrophysiology is Sound.* Biosense Webster, Inc. brochure 2007.

European Search Report Appln No. 11 19 4908 dated Mar. 7, 2012.

Japanese Notification of Reasons for Refusal dated Oct. 13, 2015 from corresponding Japanese Patent Application No. 2011-279374.

* cited by examiner

LASSO CATHETER WITH ROTATING ULTRASOUND TRANSDUCER

FIELD OF THE INVENTION

The present invention relates generally to medical probes, and particularly to catheters fitted with ultrasound transducers.

BACKGROUND OF THE INVENTION

Ablation of myocardial tissue is well known as a treatment for cardiac arrhythmias. In radio-frequency (RF) ablation, for example, a catheter is inserted into the heart and brought into contact with tissue at a target location. RF energy is then applied through an electrode on the catheter in order to create a lesion for the purpose of breaking arrhythmogenic current paths in the tissue. Recently, circumferential ablation of the ostia of the pulmonary veins has gained acceptance as a treatment for atrial arrhythmias, and particularly for atrial fibrillation. For example, U.S. Pat. No. 6,064,902, whose disclosure is incorporated herein by reference, describes a catheter for ablating tissue on the inner wall of a blood vessel, such as a pulmonary vein.

Some medical imaging systems use catheters that are fitted with ultrasound transducers. For example, U.S. Pat. No. 5,076,278, whose disclosure is incorporated herein by reference, describes an ultrasonic transducer for use in locating devices. The transducer has a curved surface, and is an annular member in shape. An elongated catheter or other device passes through the opening of the annular transducer. As another example, U.S. Pat. No. 5,081,993, whose disclosure is incorporated herein by reference, describes an ultrasonic probe that is inserted into a human organ. In some embodiments, the probe includes an annular ultrasonic transducer assembly.

SUMMARY OF THE INVENTION

An embodiment of the present invention that is described herein provides a medical device, including:

an insertion shaft, having a longitudinal axis and having a distal end adapted for insertion into a body of a patient;

a resilient end section, which is fixed to the distal end of the insertion shaft and is formed so as to define an arc oriented obliquely relative to the axis and having a center of curvature on the axis, and which has one or more electrodes disposed along the end section; and an ultrasound transducer, which is fixed to the distal end and is configured to image a vicinity of the arc using ultrasound waves.

In some embodiments, the ultrasound transducer has an annular field of view that is collinear with the axis and coincides with the vicinity of the arc. In another embodiment, the ultrasound transducer has a field of view that is inclined relative to the axis and coincides with the vicinity of the arc when the insertion shaft is rotated about the axis. The medical device may include a rotation mechanism that is configured to rotate the ultrasound transducer about the axis independently of rotation of the insertion shaft.

In a disclosed embodiment, one or more of the electrodes include ablation electrodes for ablating tissue when the end section is positioned against the tissue, and the ultrasound transducer is configured to image the ablated tissue. In an embodiment, the medical device includes a Radio Frequency (RF) generator that is coupled to supply RF energy to the ablation electrodes so as to ablate the tissue.

In an embodiment, one or more of the electrodes are configured to sense an electrical potential on cardiac tissue when the end section is positioned against the tissue. In another embodiment, the end section includes a position transducer, and the medical device includes a position sensing system that is configured to communicate with the position transducer so as to determine a position of the end section within the body.

There is additionally provided, in accordance with an embodiment of the present invention, a method for medical treatment, including:

inserting into a body of a patient a probe including an insertion shaft, having a longitudinal axis and a distal end, and a resilient end section, which is fixed to the distal end of the insertion shaft and is formed so as to define an arc oriented obliquely relative to the axis and having a center of curvature on the axis, with electrodes disposed at respective locations along the end section;

advancing the probe axially so that the end section engages a tissue in the body along the arc, causing at least some of the electrodes to contact the tissue simultaneously and ablate the contacted tissue; and irradiating a vicinity of the arc using an ultrasound transducer that is fixed to the distal end, so as to image the ablated tissue.

In some embodiments, irradiating the vicinity of the arc includes receiving an ultrasound wave that is reflected from the tissue, and producing and displaying ultrasound images of the tissue based on the reflected ultrasound wave. In another embodiment, irradiating the vicinity of the arc includes receiving an ultrasound wave that is reflected from the tissue, and estimating a characteristic of the tissue based on the reflected ultrasound wave.

The present invention will be more fully understood from the following detailed description of the embodiments thereof, taken together with the drawings in which:

DETAILED DESCRIPTION OF EMBODIMENTS

Overview

Figure 1:
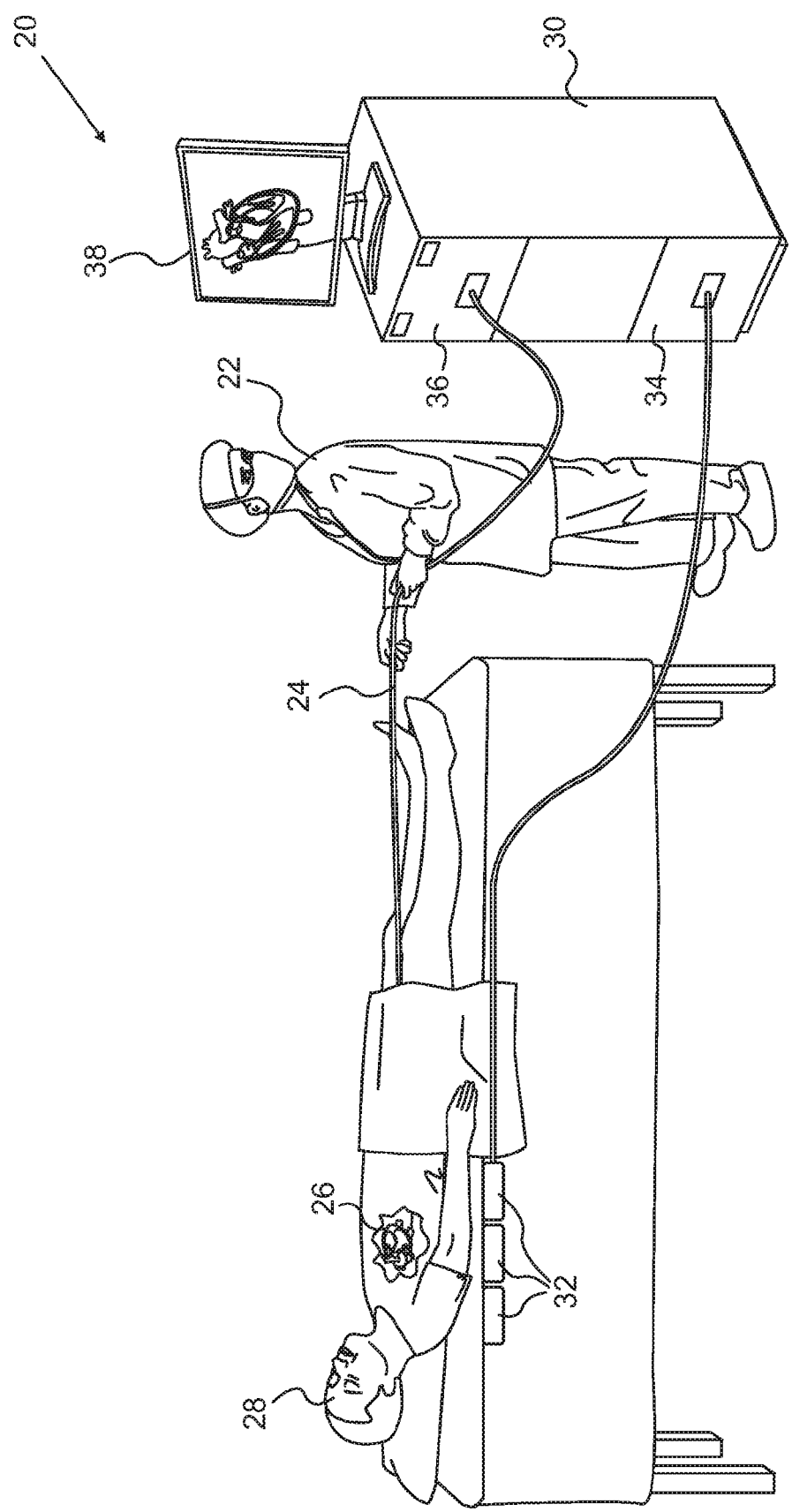
FIG. 1 is a block diagram that schematically illustrates a system for ablation and imaging in the heart, in accordance with an embodiment of the present invention.

Lasso catheters may be used for ablating tissue along an arc surrounding an anatomical structure, such as the ostium of a pulmonary vein, and/or for sensing electrical potentials at multiple points that lie on an arc. Example lasso catheters are described in U.S. patent application Ser. No. 12/649,417, filed Dec. 30, 2009, which is assigned to the assignee of the present patent application and whose disclosure is incorporated herein by reference. Lasso catheters provide an easy and reliable way to create annular lesions in the tissue, as well as sensing signals along annular paths.

Embodiments of the present invention that are described herein provide improved lasso-type medical probes, which comprise integral ultrasound transducers for imaging the treated or diagnosed tissue. In the disclosed embodiments, a medical probe comprises an insertion shaft for insertion into a body of a patient. A resilient end section is fixed to the distal end of the insertion shaft. The end section is formed so as to define an arc that is oriented obliquely relative to the longitudinal axis of the shaft. One or more electrodes, e.g., ablation electrodes and/or potential sensing electrodes, are disposed along the end section. An ultrasound transducer is fixed to the distal end of the shaft, for imaging the vicinity of the arc using ultrasound waves.

The ultrasound transducer is typically fixed to the insertion shaft such that its field of view covers the tissue that is contacted by the electrodes on the arc-shaped end section. In some embodiments, the ultrasound transducer has an annular field of view that is collinear with the longitudinal axis of the shaft. In this configuration, both the end section electrodes and the ultrasound transducer have annular geometries that complement one another. Thus, the ultrasound transducer provides simultaneous imaging of the entire annular region contacted by the catheter end section (e.g., of the arc-shaped or circumferential lesion formed by the ablation electrodes).

In alternative embodiments, the ultrasound transducer has a relatively narrow field of view that is fixed at an inclined angle relative to the longitudinal axis of the shaft. In this configuration, the ultrasound transducer images the vicinity of the arc as the shaft is rotated about its axis.

The disclosed medical probes enable physicians to perform circumferential ablation and electrical activity sensing, while at the same time imaging the tissue in question using ultrasound. The disclosed probe configurations image the vicinity of the probe's end section using an ultrasound transducer that is fixed to the same frame of reference as the probe. Therefore, the resulting ultrasound imaging focuses on the exact relevant tissue with high accuracy and resolution. Moreover, fitting both the ablation/sensing electrodes and the ultrasound transducer in the same probe reduces the cost and complexity of the procedure, enhances safety and reduces the probability of complications, and enables the entire procedure to be carried out by a single operator.

System Description

FIG. 1 is a schematic pictorial illustration of a system 20 for ablation and ultrasound imaging of tissue in a heart 26 of a patient 28, in accordance with an embodiment of the present invention. An operator 22, such as a cardiologist, inserts a catheter 24 through the vascular system of patient 28 so that the distal end of the catheter enters a chamber of the patient's heart. Operator 22 advances the catheter so that the end section of the catheter engages endocardial tissue at a desired location or locations, as shown in the figures that follow. Catheter 24 is connected by a suitable connector at its proximal end to a console 30.

The console comprises a RF generator 36 for applying RF energy through electrodes on the end section of the catheter in order to ablate the tissue contacted by the distal section. Alternatively or additionally, catheter 24 may be used for other diagnostic and/or therapeutic functions, such as intracardiac electrical mapping or other types of ablation therapy.

In the pictured embodiment, system 20 uses magnetic position sensing to determine position coordinates of the end section of the catheter inside heart 26. To determine the position coordinates, a driver circuit 34 in console 30 drives field generators 32 to generate magnetic fields within the body of patient 28. Typically, field generators 32 comprise coils, which are placed below the patient's torso at known positions external to the body. These coils generate magnetic fields in a predefined working volume that contains heart 26. One or more magnetic field sensors (not shown in the figures) within the end section of catheter 24 generate electrical signals in response to these magnetic fields.

The console processes these signals in order to determine the position (location and/or orientation) coordinates of the end section of catheter 24, and possibly also the deformation of the end section, as explained below. Console 30 may use the coordinates in driving a display 38 to show the location and status of the catheter. This method of position sensing and processing is described in detail, for example, in PCT International Publication WO 96/05768, whose disclosure is incorporated herein by reference, and is implemented in the CARTO™ system produced by Biosense Webster Inc. (Diamond Bar, Calif.).

In some embodiments, system 20 comprises an ultrasound imaging subsystem, e.g., implemented as part of console 30 or in a separate console. The ultrasound imaging subsystem uses an ultrasound transducer that is fitted in the distal end of catheter 24 for imaging the vicinity of the catheter distal end. Example catheter configurations of this sort are described in detail further below. The ultrasound imaging subsystem displays the acquired ultrasound images, e.g., on display 38.

Alternatively or additionally, system 20 may comprise an automated mechanism (not shown) for maneuvering and operating catheter 24 within the body of patient 28. Such mechanisms are typically capable of controlling both the longitudinal motion (advance/retract) and the rotation of catheter 24. In such embodiments, console 30 generates a control input for controlling the motion of the catheter based on the signals provided by the position sensing system.

Although FIG. 1 shows a particular system configuration, other system configurations may be used in alternative embodiments of the present invention. For example, the methods described hereinbelow may be applied using position transducers of other types, such as impedance-based or ultrasonic position sensors. The term "position transducer" as used herein refers to an element mounted on or in catheter 24 that causes console 30 to receive signals indicative of the coordinates of the element. The position transducer may thus comprise a receiver in the catheter, which generates a position signal to the control unit based on energy received by the transducer; or it may comprise a transmitter, emitting energy that is sensed by a receiver external to the probe. Furthermore, the methods described hereinbelow may similarly be applied in mapping and measurement applications using not only catheters, but also probes of other types, both in the heart and in other body organs and regions.

Catheter with Arc-Shaped End Section and Coincident Ultrasound Transducer

In some embodiments, the distal end of catheter 24 comprises an arc-shaped end section having multiple electrodes. This catheter configuration enables the operator to apply arc-shaped ablation patterns and/or to sense the electrical potentials on an arc-shaped path. In addition, the catheter distal end comprises an ultrasound transducer whose field of view covers the vicinity of the arc formed by the end section. The ultrasound transducer is used for imaging the tissue in question using ultrasound energy.

Figure 2B:
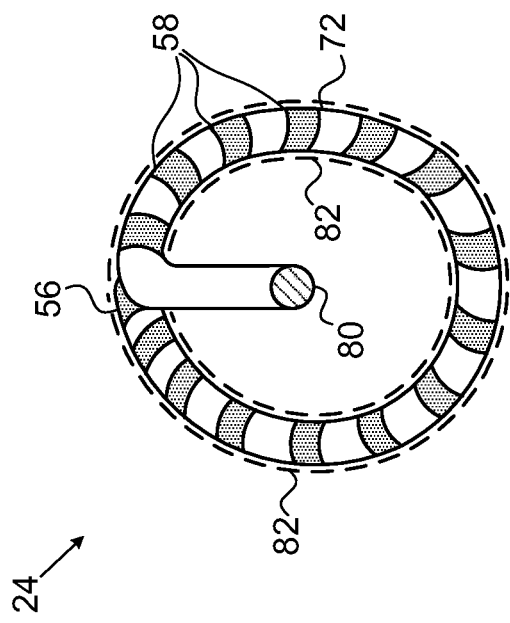
FIGS. 2A and 2B are schematic side and sectional views, respectively, of a catheter, in accordance with an embodiment of the present invention.
Figure 2A:
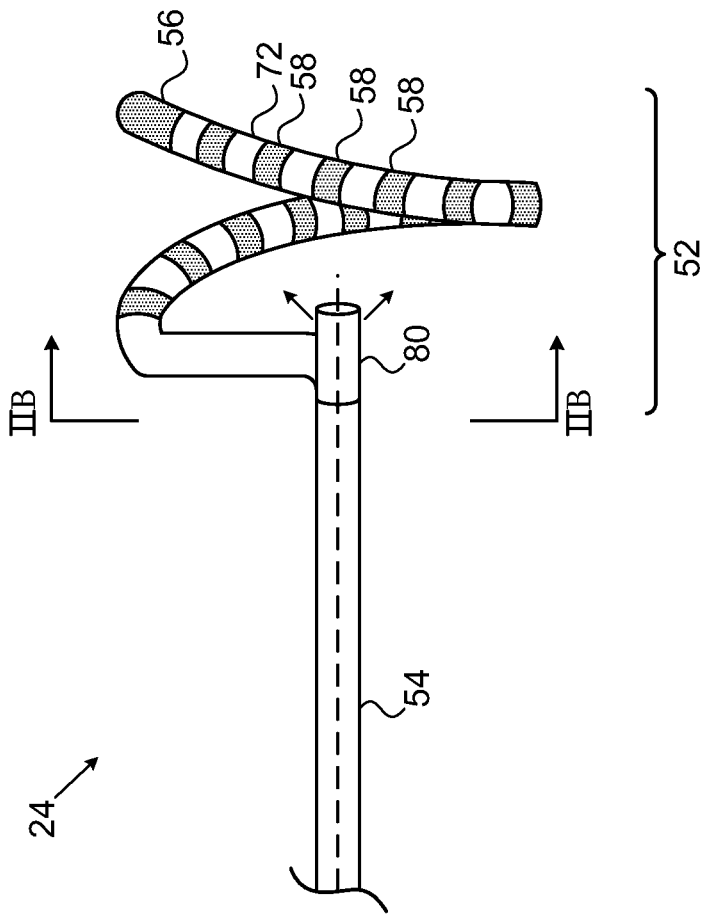

Reference is now made to FIGS. 2A and 2B, which schematically show details of the distal portion of catheter 24, in accordance with an embodiment of the present invention. FIG. 2A is a side view, while FIG. 2B is a cross-sectional view taken along a line IIB-IIB in FIG. 2A. Catheter 24 comprises an insertion shaft 54, and an end section 52 that is connected to the distal end of the insertion shaft. The Z-axis in these figures is taken to be the longitudinal axis of the insertion shaft, as illustrated by a dashed line in FIG. 2A. End section 52 is oriented roughly in the X-Y plane but has a helical form so that the distal tip of section 52 protrudes axially (along the Z-axis) in the distal direction (to the right in FIG. 2A).

Shaft 54 and end section 52 typically comprise an outer shell 72 made from a suitable flexible biocompatible material, such as polyurethane, having a diameter around 2-3 mm, with internal wires and tubing as required. In one embodiment, in which the catheter is designed for therapeutic ablation, the size of the shaft is 7 Fr (about 2.3 mm diameter), while the end section is of the same or slightly larger size (such as 7.5 Fr). In other embodiments, for diagnostic measurements, the shaft is 7 Fr, while the end section has a diameter between 1 and 2.5 mm.

End section 52 is formed as a partial or full lasso, i.e., as a preformed arcuate structure, which is centered on the axis of shaft 54 and loops through a certain angular section. In the pictured embodiment, for example, the end section comprises a full lasso loop, i.e., about 360°. In alternative embodiments, however, the catheter may comprise an arcuate end section that covers any suitable angular range, e.g., half-lasso (about 180°).

The radius of curvature of end section 52, when unconstrained, is typically between 7.5 mm and 15 mm. Because the arc structure is resilient and, possibly, slightly helical, when end section 52 is positioned in the heart (surrounding the ostium of a pulmonary vein, for example), and insertion shaft 54 is advanced distally, the end section will press against the heart tissue over the entire length of the arc, thus facilitating good tissue contact.

End section 52 comprises an array of electrodes along its length, including, in this example, a tip electrode 56 extending over the distal tip of the end section and proximal electrodes 58 distributed along the end section. The electrodes may comprise, for example, ablation electrodes, electrical potential sensing electrodes, and/or any other suitable electrode type.

Typically, the electrodes have a width between 1 mm and 4 mm, and are spaced between 1 mm and 10 mm apart. The electrodes are connected to the connector at the proximal end of catheter 24 by wires (not shown) running through the catheter. Alternatively, other electrode configurations may be used. For example, the end section may include only ring electrodes, without a tip electrode. As another example, the end section may include smaller "bump" electrodes, as described in U.S. patent application Ser. No. 12/345,720, filed Dec. 30, 2008, which is assigned to the assignee of the present patent application and whose disclosure is incorporated herein by reference. When the arc covers less than a full circle, catheter 24 may be rotated about its axis in order to ablate an entire annulus around a pulmonary vein.

Catheter 24 may also include one or more position transducers (not shown in the figure) for enabling console 30 to track both the base location and the deformation of the end section, so that the operator can verify that the end section is properly located and in good contact with the tissue. Alternatively, other types of position transducers and sensing configurations may be used in catheter 24 and system 20.

Catheter 24 comprises an ultrasound transducer 80 that is fixed to the distal end of insertion shaft 54. Any suitable type of ultrasound transducer or transducer array can be used for this purpose. Ultrasound transducers of this sort are used, for example, in ultrasound imaging catheters called SoundStar™ and AcuNav™, both produced by Biosense Webster Inc. (Diamond Bar, Calif.).

Transducer 80 is driven with suitable electrical signals by a signal generator (not shown, e.g., in console 30). In response to these signals, transducer 80 emits ultrasound waves that irradiate a predefined volume in the vicinity of end section 52. Transducer 80 receives the ultrasound energy reflected from the irradiated tissue and converts the reflected energy to electrical signals.

Based on the signals sensed by the transducer, the ultrasound imaging system (e.g., in console 30) images the vicinity of end section 52. In some embodiments, the ultrasound imaging subsystem produces ultrasound images of the tissue, and the ultrasound images are displayed to operator 22 on display 38. Operator 22 may use the ultrasound images for any suitable purpose, such as for planning an ablation procedure, or for examining the ablated tissue before, during and/or after the procedure. In alternative embodiments, the ultrasound imaging system analyzes the sensed ultrasound reflections so as to estimate tissue characteristics. Tissue characteristic estimation can be carried out before, during and/or following ablation, for example in order to assess the effectiveness of the ablation procedure. Hybrid schemes, in which the ultrasound transducer is used for both image generation and tissue characteristic estimation, are also possible.

The field of view of transducer 80 is set so as to coincide with the tissue region that is treated or diagnosed by electrodes 56 and 58 of end section 52. In the embodiment of FIGS. 2A and 2B, transducer 80 has an annular (ring-shaped) field of view. In these embodiments, the ultrasound transducer is mounted at a suitable distance along shaft 54 from end section 52, such that its field of view simultaneously covers the tissue region contacted by electrodes 56 and 58. The annular field of view of transducer 80 is shown as a dashed region 82 in FIG. 2B.

Figure 3:
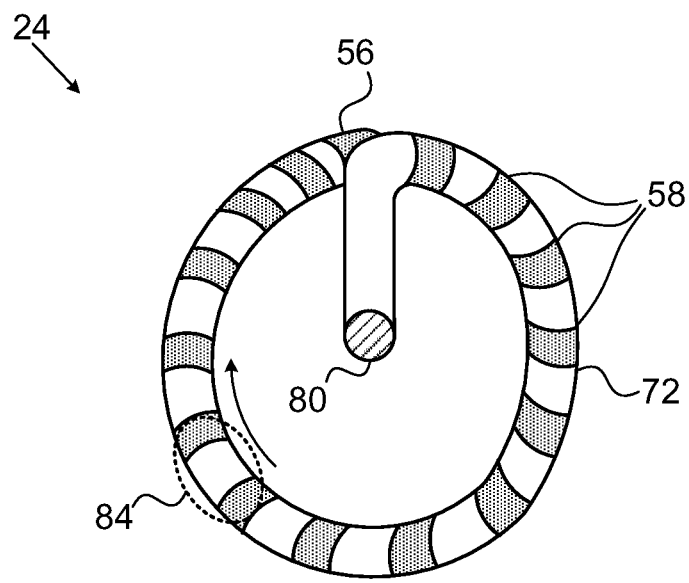
FIG. 3 is a schematic sectional view of a catheter, in accordance with another embodiment of the present invention.

FIG. 3 is a sectional view of a catheter, in accordance with an alternative embodiment of the present invention. In this embodiment, transducer 80 has a relatively narrow field of view, i.e., emits a unidirectional beam. The transducer in these embodiments is mounted in an inclined angle with respect to the longitudinal axis of shaft 54, and its field of view covers only a certain section on the arc of end section 52. The field of view of the transducer is shown in the figure as a dashed region 84.

In some embodiments, by having operator 22 rotate insertion shaft 54 about its axis, the transducer can scan the entire circumferential region that is contacted by the end section. In the example of FIG. 3, field of view 84 can scan over the entire annular region contacted by the end section electrodes by rotating the catheter about its axis.

In some embodiments, the inclined transducer does not rotate relative to the end section, i.e., both end section 52 and transducer 80 rotate together as the insertion shaft is rotated by the operator. In alternative embodiments, the transducer and the end section may be rotated separately about the longitudinal axis. For example, the insertion shaft may comprise an internal drive shaft (not shown in the figure) or other rotation mechanism that is rotated by operator 22. This drive shaft rotates the transducer without rotating the end section. Rotation of the transducer can be performed manually, or using a suitable motor.

Figure 4:
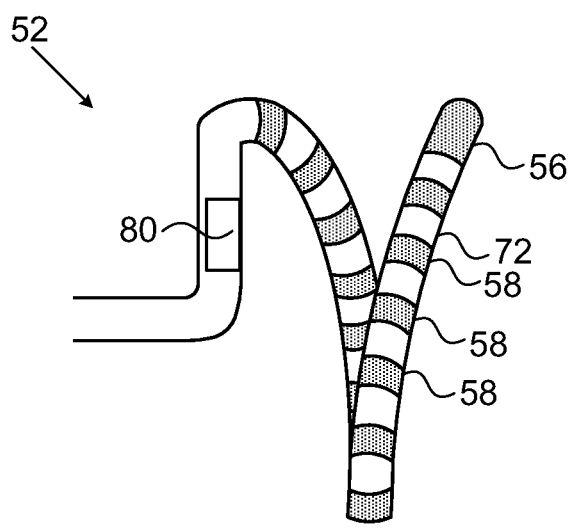
FIG. 4 is a schematic side view of a catheter, in accordance with yet another embodiment of the present invention.

FIG. 4 is a schematic side view of end section 52 of catheter 24, in accordance with yet another embodiment of the present invention. In this embodiment, ultrasound transducer 80 is located in an alternative location that is not collinear with the longitudinal axis of the catheter. Nevertheless, transducer 80 is designed and positioned such that its field of view coincides with the annular region that is contacted by electrodes 56 and 58, as explained above.

The catheter configurations shown in FIGS. 2A, 2B, 3 and 4 are example configurations that are chosen purely for the sake of conceptual clarity. In alternative embodiments, and other suitable catheter configuration can also be used. For example, an ultrasound transducer can be fitted in any other suitable catheter that applies arc-shaped ablation or sensing, in order to image the tissue in question. Although the embodiments described herein mainly address cardiac catheters, the methods and systems described herein can also be used in medical probes for other applications, such as in prostate treatment and ablation of tumors in the lever.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

The invention claimed is:

1. A medical device, comprising:
    an insertion shaft, having a longitudinal axis and having a distal end terminating in a distal tip adapted for insertion into a body of a patient;
        a resilient end section fixed to and extending from the distal tip of the insertion shaft, the resilient end section defining an arc residing in a plane, the plane oriented obliquely relative to the longitudinal axis, the arc having a center of curvature coincident with the longitudinal axis and a radius of curvature about the longitudinal axis, and which has one or more electrodes disposed along the end section;
        an ultrasound transducer, which is fixed to the distal end and is configured to image a vicinity of the arc using ultrasound waves, the ultrasound transducer having a field of view that is inclined relative to the axis and coincides with the vicinity of the arc when the insertion shaft is rotated about the axis; and
        a rotation mechanism that is configured to rotate the ultrasound transducer about the axis independently of rotation of the insertion shaft.

2. The medical device according to claim 1, wherein the ultrasound transducer has an annular field of view that is collinear with the axis and coincides with the vicinity of the arc.

3. The medical device according to claim 1, wherein one or more of the electrodes are configured to sense an electrical potential on cardiac tissue when the end section is positioned against the tissue.

4. The medical device according to claim 1, wherein the end section comprises a position transducer, and comprising a position sensing system, which is configured to communicate with the position transducer so as to determine a position of the end section within the body.

5. The medical device according to claim 1, wherein one or more of the electrodes comprise ablation electrodes for ablating tissue when the end section is positioned against the tissue, and wherein the ultrasound transducer is configured to image the ablated tissue.

6. The medical device according to claim 5, and comprising a Radio Frequency (RF) generator that is coupled to supply RF energy to the ablation electrodes so as to ablate the tissue.

7. A method for medical treatment, comprising:
    inserting into a body of a patient a probe comprising an insertion shaft, having a longitudinal axis and a distal end terminating in a distal tip, and a resilient end section fixed to and extending from the distal tip of the insertion shaft, the resilient end section defining an arc residing in a plane, the plane oriented obliquely to the longitudinal axis, the arc having a center of curvature on the longitudinal axis and a radius of curvature about the longitudinal axis, with electrodes disposed at respective locations along the end section;
    advancing the probe axially so that the end section engages a tissue in the body along the arc, causing at least some of the electrodes to contact the tissue simultaneously and ablate the contacted tissue; and
    imaging the ablated tissue by irradiating a vicinity of the arc using an ultrasound transducer that is fixed to the distal end, the ultrasound transducer having a field of view that is inclined relative to the axis and coincides with the vicinity of the arc when the insertion shaft is rotated about the axis, the probe having a rotation mechanism that is configured to rotate the ultrasound transducer about the axis independently of rotation of the insertion shaft.

8. The method according to claim 7, wherein irradiating the vicinity of the arc comprises transmitting ultrasound energy from the ultrasound transducer in an annular field of view that is collinear with the axis and coincides with the vicinity of the arc.

9. The method according to claim 7, and comprising sensing an electrical potential on the contacted tissue using one or more of the electrodes.

10. The method according to claim 7, and comprising communicating with a position transducer in the end section to determine a position of the end section within the body.

11. The method according to claim 7, wherein irradiating the vicinity of the arc comprises receiving an ultrasound wave that is reflected from the tissue, and producing and displaying ultrasound images of the tissue based on the reflected ultrasound wave.

12. The method according to claim 7, wherein irradiating the vicinity of the arc comprises receiving an ultrasound wave that is reflected from the tissue, and estimating a characteristic of the tissue based on the reflected ultrasound wave.

13. The method according to claim 7, wherein irradiating the vicinity of the arc comprises transmitting ultrasound energy from the ultrasound transducer in a field of view that is inclined relative to the axis and coincides with the vicinity of the arc when the insertion shaft is rotated about the axis.

14. The method according to claim 13, and comprising rotating the ultrasound transducer about the axis independently of rotation of the insertion shaft.

15. The method according to claim 13, and comprising supplying RF energy to the electrodes so as to ablate the tissue.

* * * * *